United States Patent [19]

Klasek et al.

[11] 4,293,367

[45] Oct. 6, 1981

[54] APPARATUS FOR EFFECTING SECUREMENT OF A TRANSVERSELY MOVED ELASTIC RIBBON TO A MOVING WEB

[75] Inventors: Ladislav J. Klasek, North Riverside; Clarence F. Lamber, Country Club Hills; Anthony Passafiume, Burbank, all of Ill.

[73] Assignee: Johnson & Johnson Baby Products Company, New Brunswick, N.J.

[21] Appl. No.: 150,516

[22] Filed: May 16, 1980

[51] Int. Cl.³ .............................................. B32B 31/08
[52] U.S. Cl. .................................... 156/494; 156/164; 156/554; 226/179; 226/180
[58] Field of Search ............... 156/164, 494, 495, 516, 156/443, 459, 554, 543, 555; 112/121.26; 2/243 R, 401, 402; 227/12; 242/158.4 R; 226/179, 180

[56] References Cited

U.S. PATENT DOCUMENTS

| | | | |
|---|---|---|---|
| 2,681,019 | 6/1954 | Liebowitz | 112/121.26 |
| 2,681,020 | 6/1954 | Liebowitz et al. | 112/121.26 |
| 2,767,937 | 10/1956 | Gisonno et al. | 242/158.4 R |
| 3,104,789 | 9/1963 | Fife | 226/180 |
| 3,235,934 | 2/1966 | Miller | 226/179 |
| 3,300,114 | 1/1967 | Jacobsen | 226/180 |
| 3,456,898 | 7/1969 | Anderson et al. | 242/158.4 R |
| 3,604,015 | 9/1971 | Dove | 2/243 R |
| 3,721,599 | 3/1973 | Addis | 156/443 |
| 3,823,049 | 7/1974 | Vetrovec | 156/443 |
| 3,828,367 | 8/1974 | Bourgeois | 2/402 |
| 3,880,696 | 4/1976 | Chen | 156/443 |
| 4,081,301 | 3/1978 | Buell | 156/164 |

Primary Examiner—Jerome W. Massie

[57] ABSTRACT

This invention relates to a method for the continuous or intermittent securing of a moving elastic member or band to a moving web or webs of disposable diaper components and the like, wherein the elastic member is moved generally transversely of its length to give the transversely moved portion a non-linear shape.

5 Claims, 12 Drawing Figures

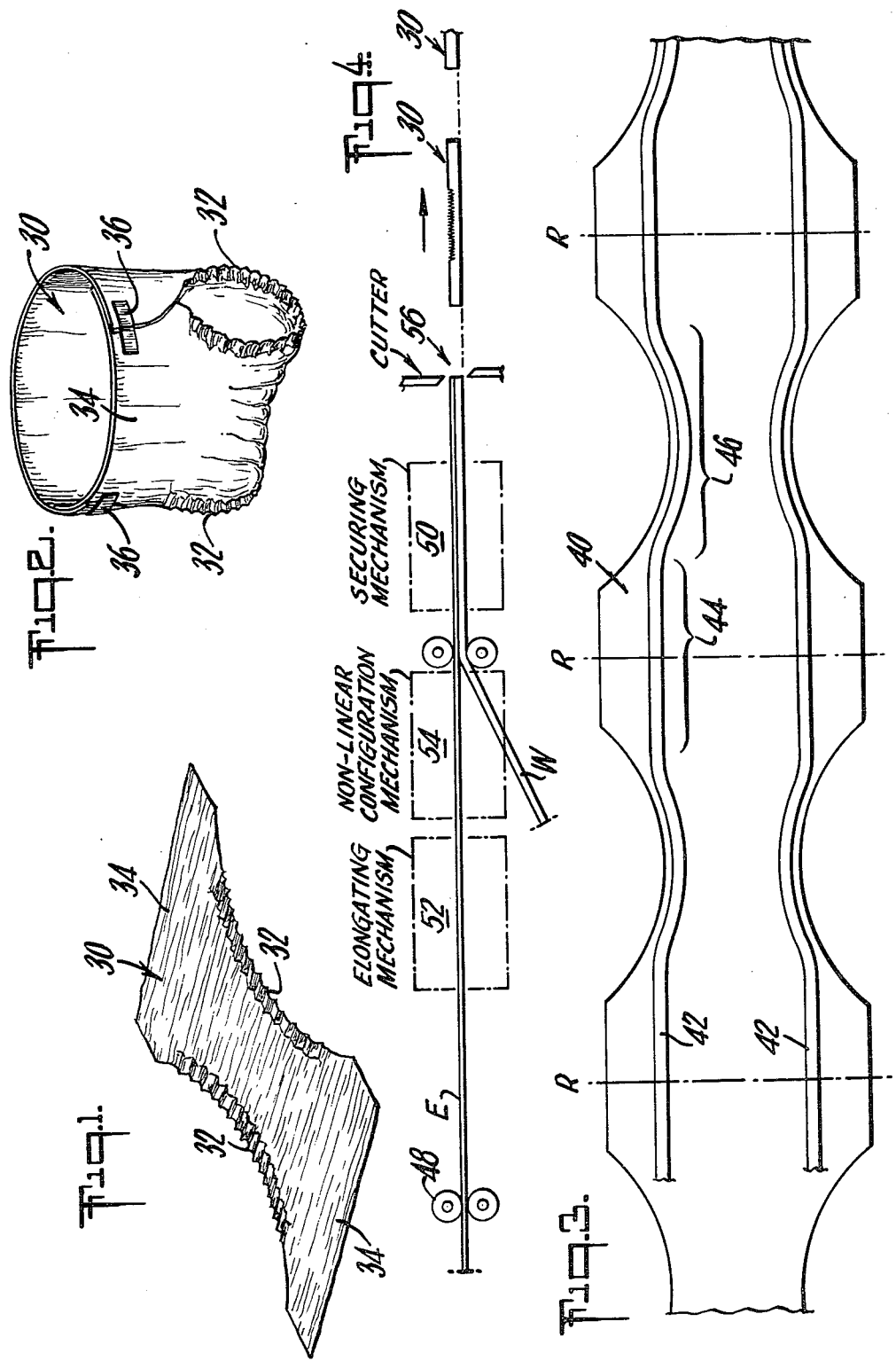

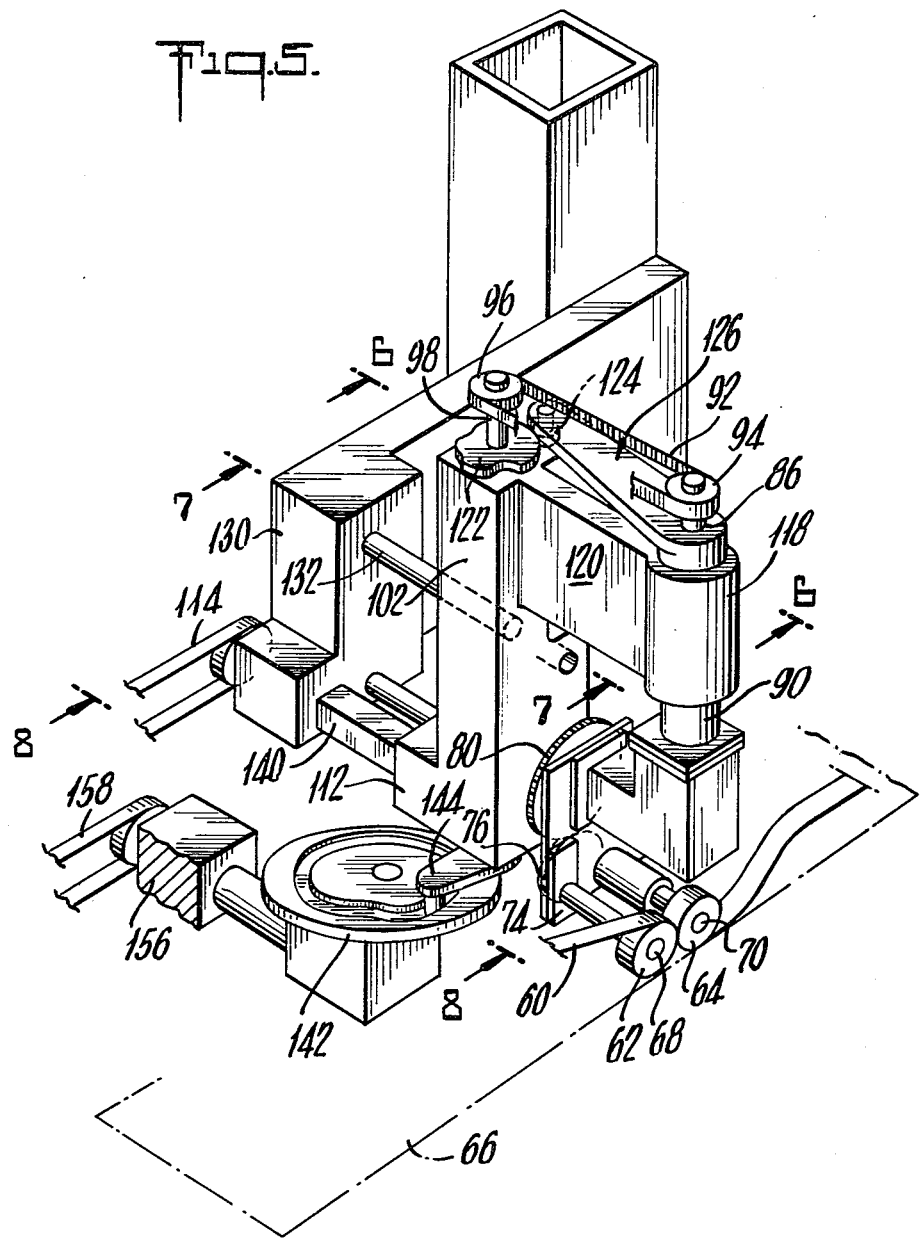

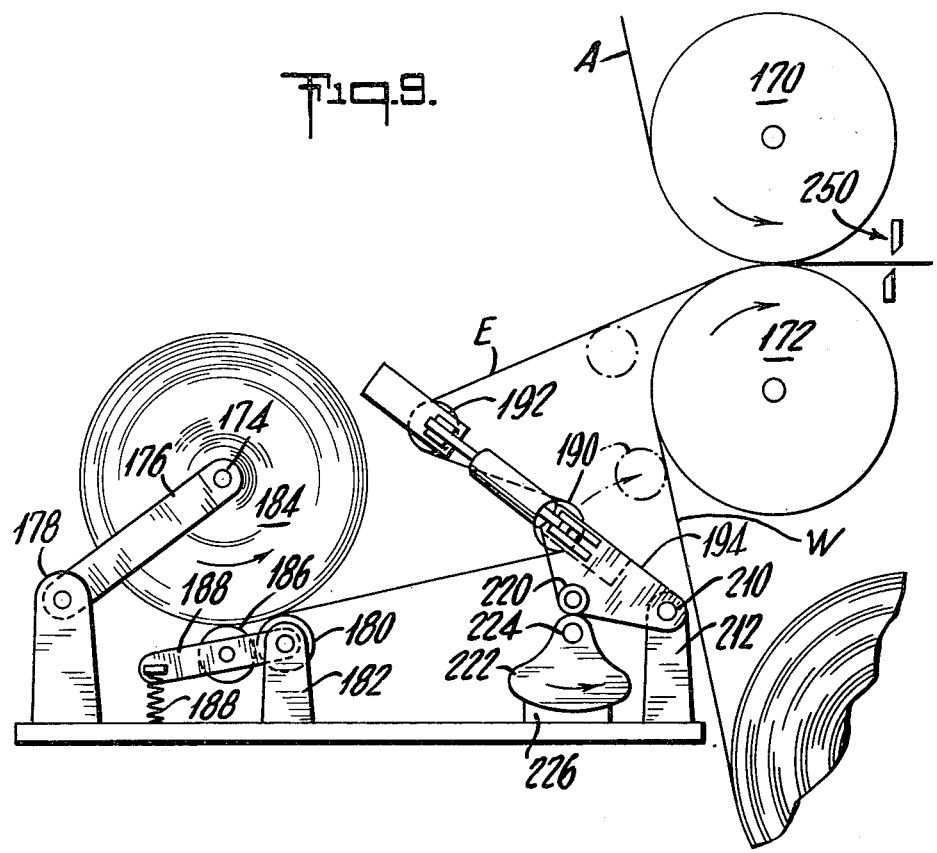
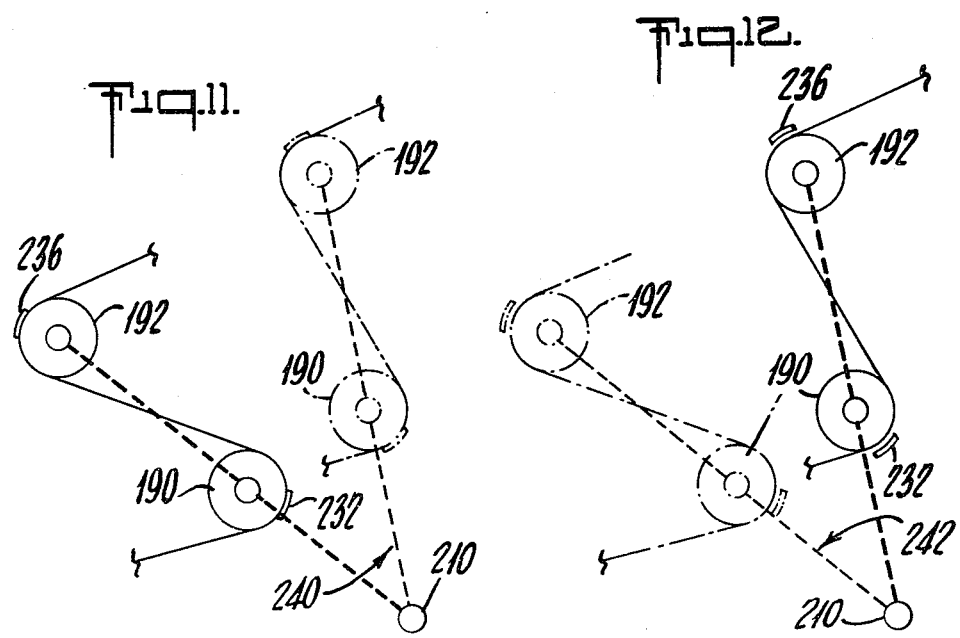

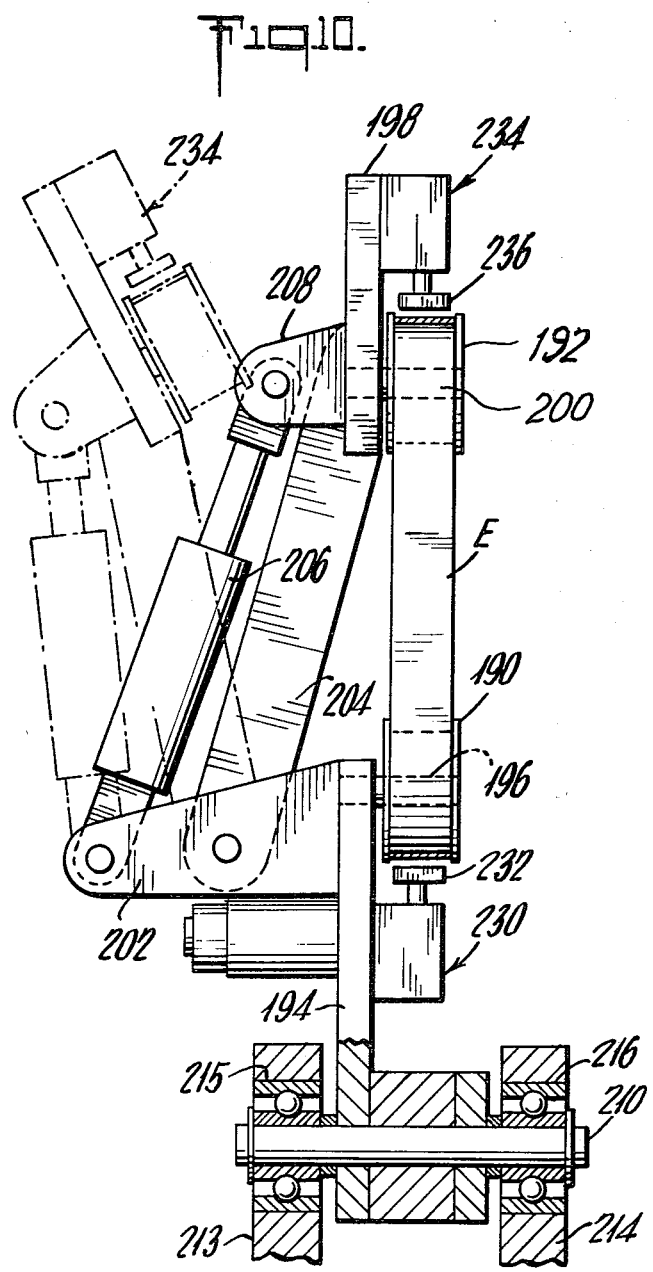

APPARATUS FOR EFFECTING SECUREMENT OF A TRANSVERSELY MOVED ELASTIC RIBBON TO A MOVING WEB

TECHNICAL FIELD

This invention relates to a method for the continuous or intermittent securing of a moving elastic member or band to a moving web or webs of disposable diaper components and the like, wherein the elastic member is moved generally transversely of its length to give the transversely moved portion a non-linear shape.

BACKGROUND OF THE INVENTION

Methods are known for fixing an elastic element or member, such as an elastomeric band or ribbon, to a flexible, substantially inelastic web of material defining clothing or compounds thereof, including briefs, panty briefs, disposable diapers, and the like.

Methods are known for applying an elastic element to a continuously moving web. The U.S. Pat. No. 3,828,367 to Bourgeois discloses a method for securing a stretched elastic element to a non-elastic fabric web and maintaining the assembled element on the web in a stretched condition until cut transversely of the direction of travel to produce separated panels. The apparatus is disclosed as including a rotating cylinder with a curved guide for imparting a non-linear configuration to the elastic element so that the ribbon follows a predetermined contour on the non-elastic fabric.

With the method disclosed in the above-discussed Bourgeois patent, the elastic thread to be laid in a non-linear configuration contains adhesive on its surface and must be of a sufficient thickness to allow the elastic thread to be compressed during application to facilitate adhesion. This thick elastic produces a thickened elastic portion in the final product. Also in the apparatus disclosed, the use of the more common liquid adhesives is not indicated as they would tend to deposit and "gum up" the guiding grooves as well as the roll surfaces.

The U.S. Pat. No. 4,081,301 to Buell cites other prior art patents showing ways in which an elastic ribbon is joined to a moving web of material. The Buell patent itself discloses a method and apparatus for continuously attaching discrete lengths of elastic ribbon to a moving web in which the elastic ribbon is fed in a stretched condition to the web and in which the elastic ribbon is intermittently secured to predetermined regions of the web while so stretched. Subsequently, the web and elastic ribbon are transversely cut in an area where the elastic ribbon is not secured to the web, thereby forming severed, unadhered portions of elastic at both ends of each discrete length of stretched elastic ribbon adhered to the web and allowing the severed, unadhered ends of the elastic ribbon to relax and contract to their unstretched state. The method disclosed in the above-discussed Buell patent provides for the elastic to be laid in a linear configuration and no technique for providing for a non-linear configuration of the elastic thread is disclosed.

In order to avoid the undesirable thickening of the area where an elastic member is inserted and to allow the use of elastic members of various configurations such as, film, ribbon, filaments, and the like, it would be desirable to provide a method and apparatus in which any type of elastic member could be laid in a non-linear configuration and secured to the moving web in that configuration.

SUMMARY OF THE INVENTION

According to the present invention, a method and apparatus is provided for securing an elastic member in a non-linear configuration to a continuously moving, flexible, generally inelastic web of material, such as material defining disposable diaper components or other apparel components, and the like, to impart a stretchable characteristic to predetermined portions of the components.

A web of the components is moved along a path to a securement zone and an elastic member is continuously fed toward the securement zone and along a face of the web. Additional sheets of material, such as an absorbent pad and an overlying sheet, are also preferably fed to the securement zone. At least a segment of the member is elongated, upstream of the securement zone, to form a stretched segment and at least a portion of that stretched segment is moved generally transversely of its length to give said portion a non-linear shape. At least the transversely moved portion of the member is secured to the web and the member subsequently severed, along with the web (and other overlying sheets as may have been applied), to create separate articles such as diapers.

In one embodiment of the method of the present invention for producing disposable diapers, the diaper components include a plurality of absorbent batts with the batts being shaped so that their longitudinal edges are non-linear. The stretched segment of the elastic member is moved generally transversely of its length so as to be disposed adjacent the non-linear longitudinal edges of the batt. In a preferred embodiment of the above-discussed method, the non-linear shape of the longitudinal edge of the batt and the non-linear shape of the stretched segment of the elastic member are substantially identical.

In certain embodiments of the present invention, the elastic member is stretched along its entire length upstream of the securement zone, and then moved transversely of its length to produce a non-linear shape and at least a segment of the transversely moved portion is secured to the web.

According to the present invention, a contoured configuration can be given to the elastic member secured to the web. To this end, at least a portion of the elastic member is moved generally transversely of its length to give the transversely moved portion a non-linear shape as it is being secured to the web or webs. In this manner, the elastic member can be secured generally along the contour of a curved leg opening in a disposable diaper.

Thus, it is seen that the present invention yields desirable and beneficial results—results which are not only new and different but which also provide a substantial improvement over the prior art.

Numerous other advantages and features of the present invention will become readily apparent from the following detailed description of the invention and of various embodiments thereof, from the claims and from the accompanying drawings.

BRIEF DESCRIPTION OF THE DRAWINGS

In the accompanying drawings forming part of the specification and in which like numerals are employed to designate like parts throughout the same, FIG. 1 is a perspective view of an unfolded disposable diaper formed in accordance with the invention;

FIG. 2 is a perspective view of the diaper illustrated in FIG. 1 shown in an orientation that would be assumed when properly placed about the body of an infant and conforming thereto;

FIG. 3 is a plan view of a moisture repellent backing sheet or web for forming interconnected disposable diapers with the absorbent pads and facing material removed to more clearly illustrate the pair of continuous elastic members adhered to the backing web (maintained under tension in accordance with the invention);

FIG. 4 is a simplified, diagrammatic illustration of the method according to the invention;

FIG. 5 is a perspective view of one embodiment of the apparatus for effecting the method of the invention;

FIGS. 9-12 are simplified diagrammatic illustration of another embodiment of the apparatus of the present invention.

DESCRIPTION OF THE PREFERRED EMBODIMENT

Figure 6:
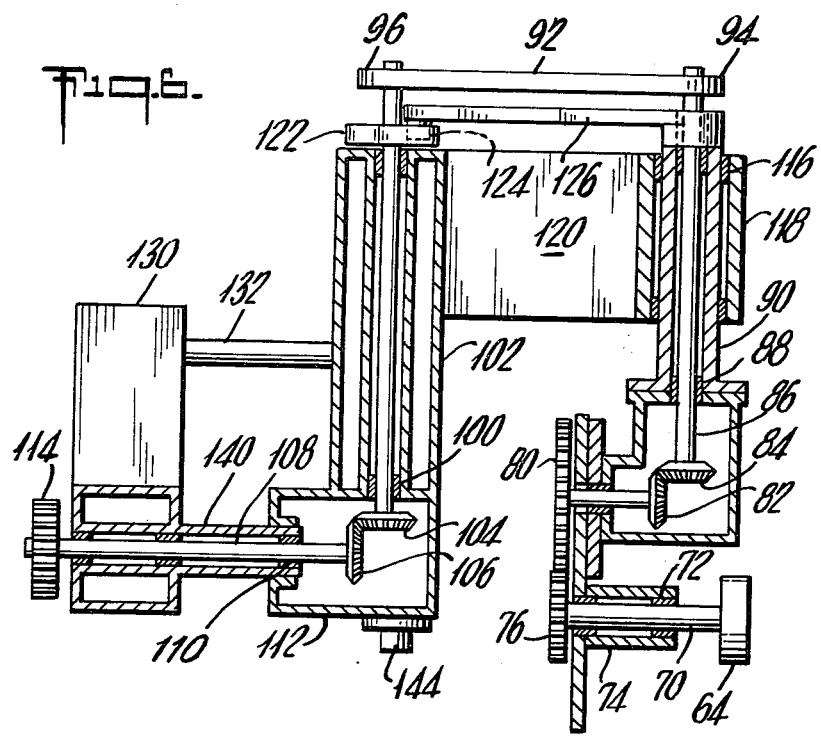
FIG. 6 is a cross-sectional view taken at plane 6—6 of FIG. 5.

The method and apparatus of the present invention may be used in many different forms. While the invention is susceptible of the embodiment in many different forms, there are shown in the drawings and will herein be described in detail preferred embodiments of the invention. It should be understood, however, that the present disclosure is to be considered as an exemplification of the principles of the invention and is not intended to limit the invention to the embodiments illustrated.

The precise shapes and sizes of the components for the embodiments of the apparatus herein described are not essential to the invention unless otherwise indicated. For ease of description, the various embodiments of the apparatus of this invention will be described in a normal operating position and terms such as lower, upper, horizontal, etc., will be used with reference to this normal operating position. It will be understood, however, that the apparatus of this invention may be manufactured, stored, transported and sold in an orientation other than the normal operating position described.

The various embodiments of the apparatus of this invention have certain conventional drive mechanisms and control mechanisms, the details of which, though not fully illustrated or described, will be apparent to those having skill in the art and an understanding of the necessary functions of such mechanisms.

Referring now to the drawings, FIG. 1 shows a disposable diaper 30, which is fabricated from flexible materials and which incorporates elasticized areas 32 which partially define leg openings between non-elasticized longitudinal edge regions 34. As illustrated in FIG. 2, when the disposable diaper 30 is placed properly about an infant, the elasticized regions 32 form a generally circular configuration about the infant's legs and, owing to the elasticity thereof, are constricted about the infant's legs to follow the specific contours of the infant's legs. The non-elasticized regions 34 extend upwardly from the infant's legs along the infant's sides and are overlapped as necessary to insure a proper fit about the infant. The diaper may be secured on each side with suitable fastening means such as strips of tape 36.

The diaper 30 may be comprised of a plurality of layers of material, such as (1) a water-impervious or water repellent sheet, (2) a water-absorbent fibrous pad, but smaller than the repellent sheet and centrally disposed thereon, and (3) an overlying facing layer of material, such is equal in dimension and coterminous with the repellent sheet and in contact therewith and secured thereto in the marginal portions of the diaper extending peripherally beyond the absorbent pad. Such a multi-layered construction, and the materials therefor, are fully described in U.S. Pat. No. 3,612,055 to Mesek, etc., which, to the extent it is consistent herewith, is incorporated by reference.

FIG. 3 shows a partially completed structure from which a plurality of interconnected diapers are formed on a production line. Specifically, a repellent sheet or moisture-impervious backing web 40 is shown as having, between each pair of reference lines R, a cutout leg opening configuration substantially of the same planar shape as that of the diaper 30 illustrated in FIG. 1. Reference lines R are shown merely to illustrate the ends of each interconnected diaper. The cutout configuration of the web 40 may be produced by well-known conventional methods which form no part of the present invention.

Secured to the backing sheet 40 are a pair of spaced apart elastic members 42. For purposes of illustration, the absorbent pad and facing layer, which would normally overlie the backing web 40, are not shown. Typically, although not necessarily, the facing layer, extending beyond the absorbent pad and in registry with the web 40, would also be secured to the elastic members 42. The backing sheet 40 is preferably also coated with lines or bands of hot melt adhesive (not shown) in a longitudinal orientation for securing the facing layer and absorbent pad to the backing sheet 40.

The elastic member 42 may be a sheet, film, ribbon or the like which is easily stretched by hand and, when stretched to less than its yield point, can recover upon release to approximately its original unstretched length or to some other length sufficiently shorter than stretched length to function satisfactorily in the disposable diaper.

Preferably, the elastic member is made from elastomeric materials such as rubber or suitable types of thermoplastic film.

The elastic member 42 need not be directly secured to the other diaper components. A reticulated film may be used for member 42 and may have a plurality of spaced apertures along its length and through which apertures the backing web and facing sheet may be secured by suitable means, such as spots of adhesive.

As illustrated in FIG. 3, the elastic member 42 extends continuously along the web 40 in alternate linear section 44 and non-linear sections 46. The non-linear sections are positioned in the central portion of the final diaper. This is the area which is positioned between the wearer's legs in use.

The non-linear sections are in a stretched condition while the linear sections may be in either a stretched or unstretched condition as desired.

According to the method of the present invention, the non-linear segment or portion 44 is secured, adhered or otherwise fixed to the web 40 (and to an overlying facing sheet). The linear segment or portions, if unstretched, may also be fixed to the web 40 (and to an overlying facing sheet).

In any case, the linear portions 44 are laid on the backing web 40 in either a stretched or unstretched condition and in a manner such that these end portions can impart no elastic character to the underlying portion of the backing web 40.

FIG. 4 illustrates, by means of a very simplified diagram, the basic method of the present invention. In particular, a web W is fed through a securing station or mechanism 50 at a predetermined linear speed. The elastic member or band E is also fed to the securing station 50 adjacent the web W. A suitable mechanism, such as a pair of co-acting drive rollers 48, may be employed as necessary to feed the member E.

Although only one member E is illustrated in FIG. 4, it is to be understood that a plurality of such elastic members may be similarly fed in parallel fashion and operated upon as will be described in detail hereinafter for one such member. Similarly, specific embodiments of the apparatus for effecting the method of the present invention will be described hereinafter with respect to the securement of a single elastic member or band and it is to be understood that two or more elastic bands may be secured by such apparatus simultaneously operating upon the bands in parallel alignment.

With continued reference to FIG. 4, the strip of elastic band E is elongated by a mechanism 52, upstream of the securing mechanism 50. The elongated elastic band is provided with a non-linear configuration by a mechanism 54. Specific embodiments of the mechanism 54 for providing the non-linear configuration will be described hereinafter.

A cutter 56 is provided downstream of the securing mechanism 50 to sever the individual articles and sever the band E.

Of course, if a disposable diaper were being fabricated according to the method of the invention as illustrated in FIG. 4, the web W would be a water repellent backing sheet and an absorbent pad and facing layer would be applied on top of the web W. The pad and facing layer would be typically secured to the web W by suitable means, such as lines of hot melt adhesive or the like, so as to sandwich the band between the backing web and the facing layer exterior of the lateral edge of the absorbent pad. The absorbent pad and facing layer are not illustrated in FIG. 4 but would typically enter the securing region or mechanism 50 on the side surface of the elastic band opposite from the web W.

Various embodiments of the mechanisms for imparting a non-linear configuration to the elastic member will next be described along with various forms of the method of the present invention for applying such an elastic member to a flexible web.

Figure 8:
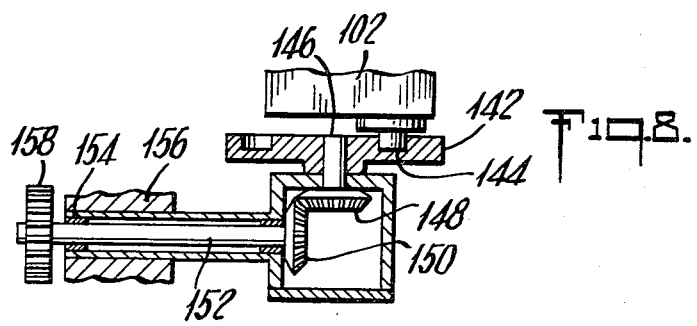
FIG. 8 is a cross-sectional view taken at plane 8—8 of FIG. 5.
Figure 7:
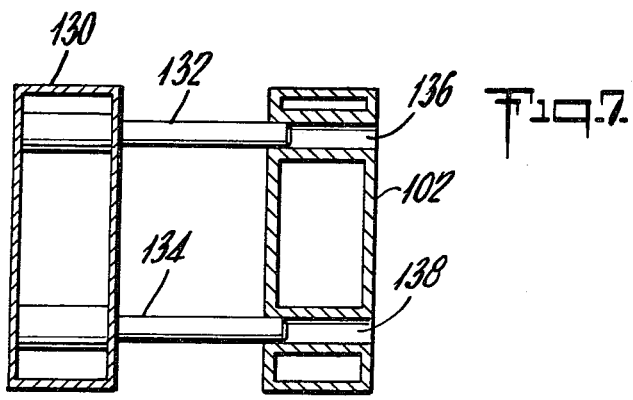
FIG. 7 is a cross-sectional view taken at plane 7—7 of FIG. 5.

In the embodiment illustrated in FIGS. 5 through 8, an elastic ribbon 60 or member is fed from a suitable supply roll (not shown for the sake of clarity) to a pair of first nip rolls travelling at a given speed (also not shown for the sake of clarity). The elastic member is fed to a second pair of nip rolls of depositing rolls 62 and 64 traveling at a faster speed than the first pair and which position the elastic member onto the surface of a web 66 passing beneath the said nip rolls. The web has had adhesive material previously applied to its surface in a manner so as to contact the elastic member as it is being applied.

One technique for applying the adhesive material is to apply a plurality of parallel longitudinal lines to the web with the lines spaced sufficiently close to one another that at least two lines contact the elastic member along its entire length. It will not be the same two lines of adhesive that contact the member along its entire length but the specific lines will vary in accordance with the configuration of the elastic member as it is disposed on the web.

The depositing rolls 62 and 64 are driven at a speed such as to stretch the elastic member a pre-designed amount just prior to applying the elastic member to to the web. The depositing rolls are mounted on a pair of shafts 68 and 70. These shafts are mounted for rotation in bearings 72 mounted from frame 74. Mounted at the opposite end of each shaft are intermeshing gears 76. Mounted above these shafts with its axis parallel to these shafts is another shaft 78. This shaft 78 is more clearly shown in FIG. 6. Mounted at one end of the shaft is a gear 80 for driving the shafts on which the depositing rolls are mounted. Mounted on the opposite end of the shaft is a tapered gear 82 which intermeshes with another tapered gear 84 to form a right angle drive. The second tapered gear 84 is mounted at the bottom of a vertical shaft 86. The vertical shaft is mounted for rotation in bearings 88 mounted in the frame portion 90. This vertical shaft is driven by a timing belt 92 positioned about a suitable timing gear 94 mounted on the top of the vertical shaft. The timing belt connects to a similar timing gear 96 mounted at the top of a second parallel vertical shaft 98 spaced a distance from the first vertical shaft. The second shaft is mounted in bearings 100 mounted in a frame member 102. Mounted at the bottom of the shaft is a tapered gear 104 which intermeshes at right angles to another tapered gear 106 to form another right angle drive. The second tapered gear 106 is mounted on a shaft 108 mounted for rotation in bearings 110 in the frame member 112. This shaft is driven by a suitable motor driving belt 114 arrangement. This combination of the two mounted shafts in spaced apart frames, coupled with the two right angle drives, provide the appropriate drive and rotation to the depositing rolls and places the elastic member on the web at a constant speed. In applying the elastic to the web in a non-linear configuration, the elastic is applied in a straight line followed by a gentle curvilinear line inwardly depending on the size of the panel adjacent to which the elastic is being applied followed by another, usually smaller, straight line and then a gentle curvilinear line outwardly and the configuration repeated. In depositing the elastic on the gentle curve, the depositing rolls 62 and 64 themselves should follow the gentle curve and lay the elastic down. The axis of the rolls should stay approximately perpendicular to the desired line of deposition of the elastic in order to lay the elastic uniformly and not have the elastic become skewed on the rolls. To provide this motion to the depositing rolls; that is, a gentle inward tilt where appropriate and a gentle outward tilt where appropriate, the first vertical shaft 86 is mounted for rotation in bearings 116 mounted in a hollow shaft 118. The hollow shaft is mounted from the framing 102, holding the second vertical shaft 98, by frame arm 120. This configuration allows the first vertical shaft as well as its bottom right angle drive and the necessary gearing and shafts holding the depositing rolls to pivot about their central vertical axis. The desired degree of pivot and timing of the pivot is accomplished by mounting a suitable cam 122 on the second vertical shaft.

Along with the cam, a movable cam follower 124 is mounted from the framing holding the second vertical shaft. A connecting shaft 126 is stationarily mounted between the cam follower and the framing holding the first vertical shaft. The cam has a slight indentation at one point to tilt the first vertical shaft and the depositing rolls in one direction and a bulge at another point to tilt the first vertical shaft and the depositing rolls in the opposite direction. In operation, the first vertical shaft continuously rotates to provide the desired drive and motion to the depositing rolls and the entire shaft mechanism and depositing rolls pivot about their vertical axis at the desired times.

To provide the desired non-linear movement to the elastic; that is, the gentle inwardly lay and the gentle outwardly lay of the elastic member, a third motion is required. This motion is to actually move the unwound rolls in a transverse direction to the longitudinally moving web. This is accomplished by mounting the entire motions described above from a stationary frame 130. As is more clearly shown in FIG. 7, the framing 102 housing the second vertical shaft 98 and holding all of the other parts previously described is movably mounted on dowels 132 and 134 attached to the stationary frame. The frame 102 is provided with openings 136 and 138 for accepting the dowels of the stationary frame. This allows the second shaft 98 and its connected parts to move inwardly and outwardly from the stationary frame 130 on the dowels 132 and 134. This motion moves the first vertical shaft and the depositing rolls as well. To allow for the above-described inward and outward motion the right angle gear driving the second vertical shaft 96 is mounted on a spline shaft 140 which allows the rotating shaft 108 to be moved with respect to the stationary housing 130.

The inward-outward movement of the combined vertical shafts and depositing rolls is controlled by a circular cam 142 which matches with a follower 144 mounted on the framing 102 of the second vertical shaft 98. As is more clearly shown in FIG. 8, the cam is mounted for rotation on a shaft 146. At the bottom of the shaft is a tapered gear 148 which mixes with a second tapered gear 150 to form a right angle drive. The second tapered gear 150 is mounted on a shaft 152 mounted for rotation in bearings 154 mounted in frame member 156. The shaft 152 is driven by a suitable belt and motor drive 158. The cam has a configuration such as to control the inward and outward motion of the combined vertical shafts and depositing rolls.

The cam 144 is timed with the cam 122 and cam follower 124 mounted at the top of the second vertical shaft 98 to synchronize the skewing of the first vertical shaft and the depositing rolls with the inward and outward movements and deposit the elastic in the desired non-linear configuration.

Another embodiment of the apparatus of the present invention is illustrated in FIGS. 9, 10, 11 and 12. The apparatus operates to apply alternately stretched and unstretched segments of an elastic member or band to a moving web wherein portions of the band are moved generally transversely of the band length to give a non-linear shape to the band as it is attached to the web. A web W passes upwardly to and between a pair of driving pinch rolls 170 and 172. Additional layers, such as layer A, may be fed from above between the pinch rolls while the elastic band E is fed to the pinch rolls between layer A and the web W.

The elastic band E may be wound about a spool 174 which is rotatably mounted to arm 176 which is in turn pivotally mounted to support member 178. A rotatably mounted driving roll 180 is mounted to a support 182 for engaging the outermost layer of band E on the roll 184. To prevent an overdrive condition, a friction brake mechanism may be employed, such as the brake roll 186 rotatably mounted to arm 188 which in turn is pivotally mounted at one end to support 182 and which is biased at the opposite end toward the roll 184 by suitable means, such as spring 188. The brake roll 186 is constantly engaged with the driving roll 180 and is thus rotated in the direction opposite from the roll. By appropriate adjustment of the spring 188, the brake roll 186 may be forced to a greater or lesser extent as desired, against the roll 184 to apply a constant resistance to the rotation of the roll 184 and thus act to prevent a peripheral speed greater than the peripheral speed of the driving roll 180.

Downstream of the driving roll 180, the elastic band E is threaded partially around a first, lower stretch roll 190 in a first direction and partially around a second stretch roll 192 in a second direction. As best illustrated in FIG. 10, the first stretch roll 190 is rotatably mounted to a rocker arm 194 about pin 196. The upper or second stretch roll 192 is mounted to an upper plate 198 by means of shaft 200 and the upper plate 198 is pivotally mounted to an extension 202 on the rocker arm 194 by means of link 204. As best illustrated in FIG. 10, the upper plate 198 and second stretch roll 192 are movable between a first position illustrated in solid line and a second, moved position illustrated in dashed line by means of a piston/cylinder operator 206, one end of which is pivotally attached to a lug 208 on the plate 198 and the other end of which is pivotally attached to the extension 202 on the rocker arm.

Extension of the piston/cylinder operator 206 in the orientation shown in solid lines in FIG. 10 urges the second stretch roll 192 into a generally vertical plane coincident with the first or lower stretch roll 190. In that position, the second stretch roll shaft 200 is parallel to the first stretch roll shaft 196. When the piston/cylinder operator 206 is retracted to the position shown in dashed lines in FIG. 10, the second stretch roll 192 is necessarily moved transversely of the path of the elastic band E and web W and the orientation of the second stretch roll shaft 200 necessarily tilts or becomes skewed with respect to the first stretch roll shaft 196.

The rocker arm 194, which carries both the first and second stretch rolls is fixed to shaft 210 which is pivotally mounted to a support post 212. Post 212 has bifurcated end portions 213 and 214 and receiving bearings 215 and 216, respectively, through which the shaft 210 is mounted for rotation.

As illustrated in FIG. 9, rocker arm 194 carries a cam follower or roller 220 which is adapted to engage a rotating cam 222 mounted to shaft 224 and supported for rotation on post 226. The shaft 224, and hence cam 222, are rotated at a constant angular velocity by a suitable means (not illustrated). Rotation of cam 222 causes the rocker arm 194 to swing or oscillate in an arc about the axis of shaft 210 toward and away from the pair of pinch rolls 170 and 172. This has the effect of elongating or relaxing the elastic band E extending between the stretch rolls 190 and 192 and the pinch rolls.

In order to maintain alternating stretched and unstretched segments of elastic band E as they are fed into the pinch rolls 170 and 172 an intermittently actuated braking or arresting system is provided. Specifically, a first brake means 230 is mounted to rocker arm 194 below the first stretch roll 190 and has a brake pad 232 which is adapted to be reciprocated between an extended position in contact with the band on roll 190 and a retracted position out of contact with the band E. Similarly, a second brake means 234 is mounted on the upper plate 198 and has a brake pad 236 adapted to be moved between an extended position in contact with the band E on roll 192 and a retracted position out of contact with the band E. The brake pads may be reciprocated between their extended and retracted positions by suitable conventional means, such as electric solenoid operators, pneumatic piston/cylinder operators, etc.

FIG. 11 illustrates the movement of the first and second stretch rolls 190 and 192 from the position furthest from the pair of pinch rolls 170 and 172 to the position closest to the pinch rolls. This movement is effected by the cam 222 causing the rocker arm 194 to swing in the direction of arrow 240. Immediately before this movement is initiated, and until the movement is terminated, the brakes 232 and 236 are applied to the rolls 190 and 192 respectively. Thus, as the rolls 190 and 192 are swung to the position closest to the pinch rolls, the linear distance through which the band E must travel before entering the pinch rolls is reduced. This has the effect of relaxing a previously stretched band to form an unstretched segment of band.

Conversely, as the cam rotates further, the rocker arm 194 swings back away from the pair of pinch rolls 170 and 172 as best illustrated in FIG. 12. At the initiation of this return movement, and until the stretch rolls have been moved to the position furthest from the pinch rolls in the direction of arrow 242, the brakes 232 and 236 are released. This allows the elastic band to continue feeding forward to the pinch rolls 170 and 172 even though the elastic band is being stretched. The movement of the stretch rolls illustrated in FIG. 12 thus elongates the elastic band and forms a stretched segment.

To provide the desired contoured configuration of the elastic band secured to the web, the piston/cylinder operator 206 (FIG. 10) is intermittently actuated. Of course, the movement of the piston/cylinder operator 206 is appropriately timed with the moving web to produce the desired configuration. It should also be noted that if desired, the first or lower stretch roll 190 could be mounted to an extension of the upper support member 198 (instead of to the lower support member 194 illustrated) so as to permit the lower roll 190 to tilt with the upper or second roll 192.

The band E is secured over all or a portion of its length to the web W by suitable means as previously described. For simplicity, such securing means have not been illustrated for this embodiment in FIGS. 9-12. Further, the assembled layer A, elastic band E, and web W may be severed downstream of the pair of rolls 170 and 172 at suitable intervals to form individual articles, such as diapers, by means of appropriate severing mechanism 250 illustrated in FIG. 9.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

We claim:
1. An apparatus for securing an elastic member to a flexible web of material in a non-linear configuration, said apparatus comprising:
 (a) a pair of rotatable depositing rolls adapted to deposit said elastic member on a web, said web traveling in a fixed path beneath said depositing rolls;
 (b) means for rotating said depositing rolls in opposite directions and at the same linear peripheral speed to deposit said elastic member on the surface of said web;
 (c) means for skewing said depositing rolls with respect to the fixed path to which the web is traveling; and
 (d) means for moving said depositing rolls transverse of the direction in which said web is traveling.

2. An apparatus in accordance with claim 1 wherein the means for skewing said depositing rolls includes a cam and cam follower for alternately skewing the rolls first in one direction and then in the opposite direction.

3. Apparatus in accordance with claim 1 wherein the means for moving said depositing rolls in the transverse direction comprises a cam and cam follower for alternately moving said rolls in a first transverse direction and then in the opposite direction.

4. Apparatus in accordance with claim 3 wherein the means for skewing said depositing rolls includes a cam and cam follower for alternately skewing the rolls first in one direction and then in the opposite direction.

5. An apparatus for securing an elastic member to a flexible web of material in a non-linear configuration, said apparatus comprising:
 (a) a pair of rotatable depositing rolls adapted to deposit said elastic member to the surface of a web traveling in a fixed path beneath said depositing rolls;
 (b) a pair of spaced apart vertical shafts;
 (c) a right angle drive at the bottom of each vertical shaft;
 (d) a frame member from which the first of said vertical shafts is mounted;
 (e) a gear train connecting the right angle drive of the first vertical shaft to the depositing rolls;
 (f) means for driving the right angle drive at the second of said vertical shafts;
 (g) a pair of timing gears mounted at the top of said vertical shafts;
 (h) a timing belt connecting said timing gears for imparting drive from the second vertical shaft to the first vertical shaft;
 (i) a cam mounted at the top of the second vertical shaft;
 (j) a cam follower cooperating with said cam and being linked to said frame member to skew the frame member and hence the first vertical shaft and the depositing rolls with respect to said flexible web of material;
 (k) slidably movable frame means from which the second vertical shaft, its right angle drive, and the frame member are mounted;
 (l) a second cam follower mounted from said frame means;
 (m) a rotatable cam cooperating with said cam follower; and
 (n) means for rotating said cam to move the frame means and hence the first vertical shaft and the depositing rolls in a transverse direction with respect to the path of the web material.

* * * * *